United States Patent [19]

Faupel et al.

[11] Patent Number: 5,082,548

[45] Date of Patent: * Jan. 21, 1992

[54] ISOELECTRIC FOCUSING APPARATUS

[75] Inventors: Daniel M. Faupel, Kingersheim, France; Pier G. Righetti, Milan, Italy

[73] Assignee: Ciba-Geigy Corporation, Ardsley, N.Y.

[ * ] Notice: The portion of the term of this patent subsequent to Nov. 20, 2007 has been disclaimed.

[21] Appl. No.: 577,421

[22] Filed: Sep. 4, 1990

Related U.S. Application Data

[63] Continuation of Ser. No. 179,619, Apr. 8, 1988, Pat. No. 4,971,670.

[30] Foreign Application Priority Data

Apr. 11, 1987 [GB] United Kingdom ............... 8708746
Dec. 3, 1987 [GB] United Kingdom ............... 8728289

[51] Int. Cl.$^5$ ............................................. G01N 27/26
[52] U.S. Cl. ................................. 204/299 R; 204/301; 204/183.2
[58] Field of Search ................. 204/299 R, 301, 183.2

[56] References Cited

U.S. PATENT DOCUMENTS

| | | | |
|---|---|---|---|
| 3,539,493 | 11/1970 | Dorman | 204/299 R |
| 3,844,925 | 10/1974 | Stathakos | 204/299 R |
| 4,243,507 | 1/1981 | Martin et al. | 204/301 |
| 4,334,972 | 6/1982 | Säderberg | 204/180.1 |

FOREIGN PATENT DOCUMENTS

| | | |
|---|---|---|
| 103965 | 3/1984 | European Pat. Off. |
| 323948 | 7/1989 | European Pat. Off. |

OTHER PUBLICATIONS

Righetti, P. G. "Immobilized pH Gradients: Recent Developments." in: Jorgenson et al., *New Directions in Electrophoretic Methods* (Wash., D.C., American Chemical Society, 1987), pp. 33–35.
Wenger et al. J. Biochem. Biophys. Methods, vol. 14 pp. 29–43 (1987).
Faupel et al. J. Biochem. Biophys. Methods, vol. 15, pp. 147–162 (1987).
Righetti et al. J. Biochem. Biophys. Methods, vol. 15, pp. 163–176 (1987).
Barzaghi et al. J. Biochem. Biophys. Methods, vol. 15, pp. 177–188 (1987).
Righetti et al. J. Biochem. Biophys. Methods, vol. 15, pp. 189–198 (1987).
Faupel et al. J. Chromatography vol. 238 pp. 226–231 (1982).

*Primary Examiner*—John Niebling
*Assistant Examiner*—David G. Ryser
*Attorney, Agent, or Firm*—Irving M. Fishman; JoAnn Villamizer

[57] ABSTRACT

Figure 1:
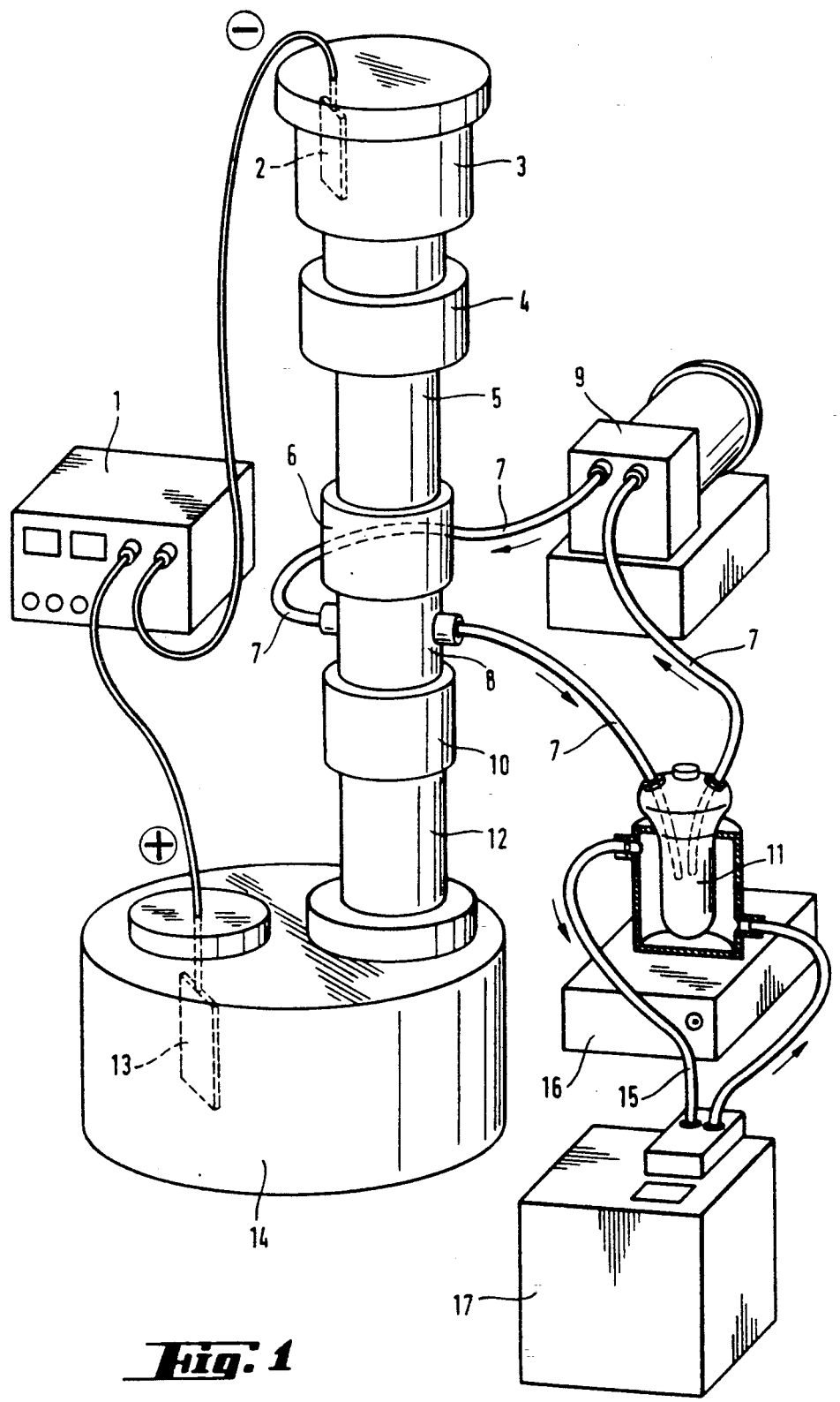

Described is an isoelectric focusing electrophoretic process for the separation and purification of an amphoteric or neutral chemical compound from one or more electrically charged chemical compound(s). Said process is illustrated below at the example of the purification of a protein from contaminating proteins and salts. It may be carried out in an apparatus especially designed therefor, e.g. an apparatus as depicted in FIG. 1. Said apparatus and various modifications thereof are also claimed. The mixture to be separated is present within a hydraulic flow in chamber 8. Cylinders 5 and 12 contain immobilized pH-gradients or are replaced by amphoteric isoelectric pH-membranes. Each of said pH-gradients and pH-membranes has conductivity and both buffering and titrant capacity in its pH-interval. The extremities of said gradients or pH-membranes forming the ceiling and the floor of chamber 8 have isoelectric points equal to or just higher and just lower than the isoelectric point of the protein of interest which is kept at its isoelectric point in the hydraulic flow and does not enter said pH-gradients and pH-membranes. Contrary thereto the contaminating proteins and salts are driven by an electric field into said pH-gradients or via said pH-gradients or pH-membranes into the electrolyte reservoirs 3 and 14. The described process has the advantage that the desired compound need not be detected and extracted from any matrix, e.g. from said pH-gradients, and that the recovery and purity of the desired compound is higher.

21 Claims, 10 Drawing Sheets

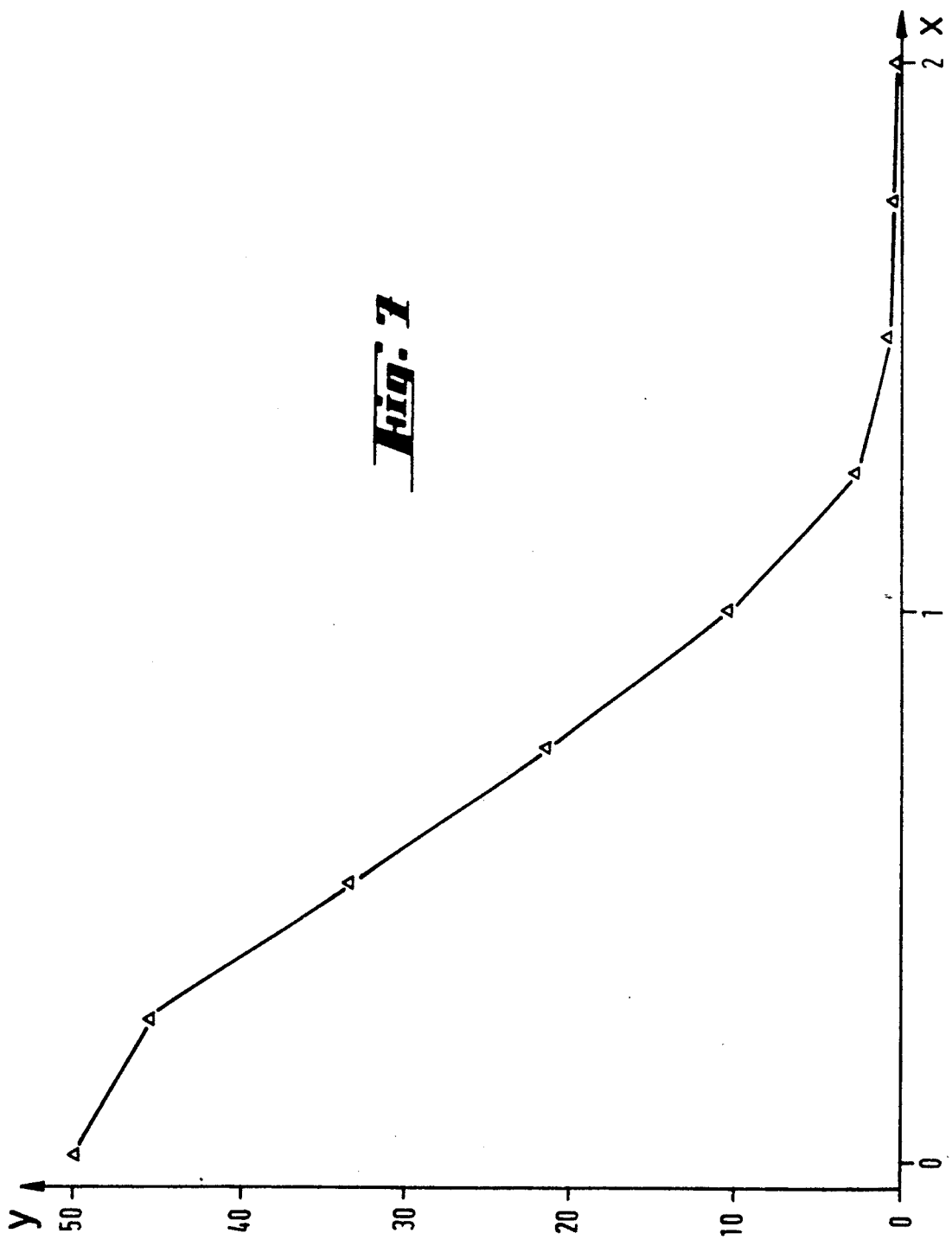

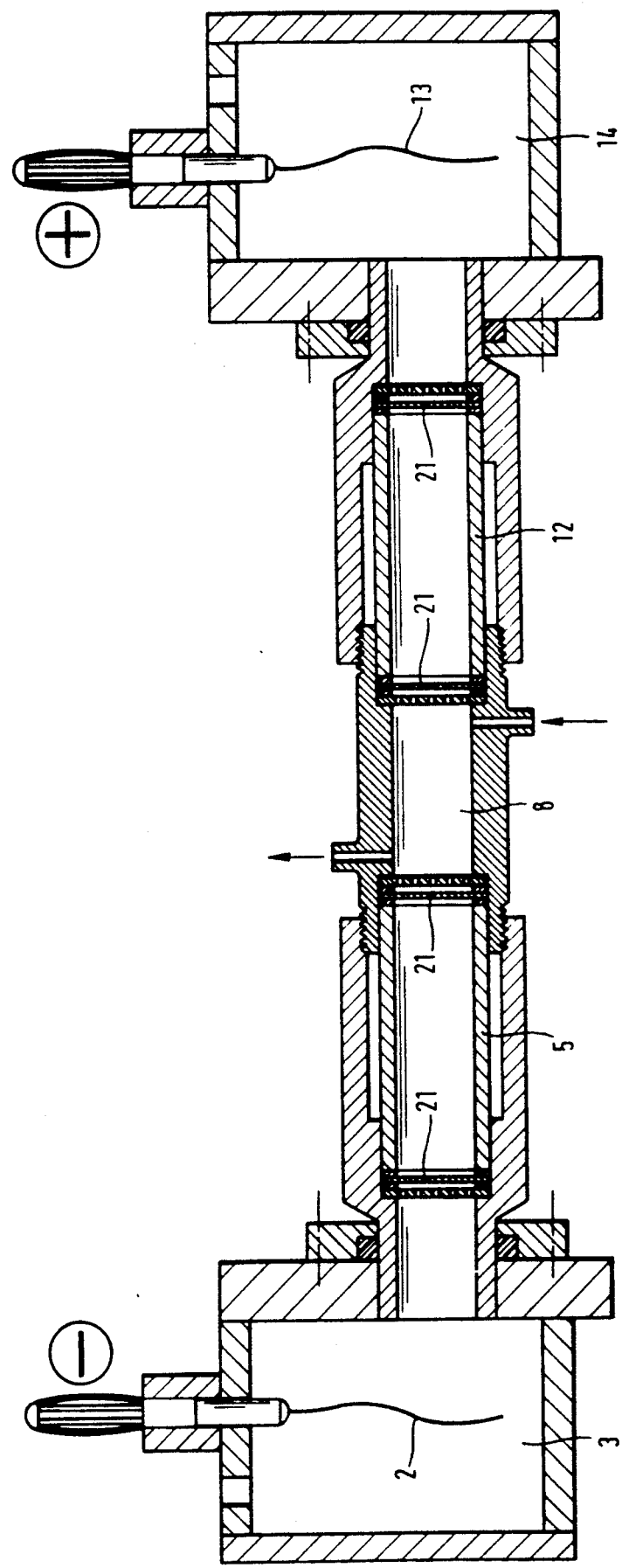

ISOELECTRIC FOCUSING APPARATUS

This is a continuation of application Ser. No. 179,619 filed on Apr. 8, 1988 now U.S. Pat. No. 4,971,670.

The present invention relates to a new and inventive process for separating chemical compounds, e.g. peptides and proteins, having a zero net electrical charge or being neutral under the experimental conditions used, from other amphoteric or non-amphoteric chemical compounds, e.g. other peptides, proteins and/or salts, having a net electrical charge under said same experimental conditions by electrophoresis, especially preparative isoelectric focusing, and to a new means, i.e. an apparatus, for carrying out said process.

Preparative electrophoresis is a known technique and various forms of electrophoresis apparatus have been proposed for both analytical and preparative purposes. Basically, the instrumentations and principles for preparative electrophoresis can be classified into four main classes, according to the electrophoretic principle utilized [cf. A. T. Andrews, Electrophoresis: Theory, Techniques, and Biochemical and Clinical Applications, Clarendon Press, Oxford 1986]:

a) disc electrophoresis
b) free curtain electrophoresis
c) isotachophoresis and
d) isoelectric focusing [cf. P. G. Righetti, Isoelectric Focusing: Theory, Methodology and Applications, Elsevier, Amsterdam, pp. 204-207 (1983)].

In general, disc electrophoresis and isotachophoresis are run in hydrophilic matrices, either continuous (agarose and polyacrylamide) or discontinuous (granulated beds, such as Sephadex ®). They are characterized by a high resolving power, but low tolerated sample loads. Free curtain electrophoresis in general utilizes continuous buffers, is performed in a free liquid phase and is characterized by a continuously flowing thin film of buffer with a continuous sample input. Basically this technique offers large sample handling capacities but low resolution. In addition, due to the higher diffusion coefficient of proteins, this method is mostly confined to purification of intact cells or subcellular organelles.

Isoelectric focusing (IEF) can be performed either in liquid supports (density gradients) or in gel media, either continuous or granulated. In fact, the technique of IEF was initiated as a preparative methodology, utilizing vertical glass columns filled with a sucrose density gradient. Moderately high sample loads could be handled with a high resolving power ($\Delta pI=0.02$ of a pH unit; pI=isoelectric point), which was, however, severely lost when emptying the column via the bottom harvesting funnel. This technique has in fact today been essentially abandoned in favor of IEF in gelatinous supporting media (mostly agarose and polyacrylamide matrices). The latter allows a high resolving power, but only moderate protein loads. In addition, all preparative techniques which utilize as anticonvective media hydrophilic gels have the problem of recovering the purified protein from the matrix. This requires additional handling steps, e.g. detection of the zone of interest, band cutting and elution by diffusion or electrophoretic recovery. That has two major disadvantages: a) low recoveries, as any matrix tends to irreversibly adsorb proteins; and b) the possibility of contamination from gel material (especially in the case of synthetic supports, such as polyacrylamide, contamination from unreacted monomers and from short, oligomeric polyacrylamide coils non-covalently grafted to the bulk matrix).

The present invention is based on the task to provide a process for the purification of chemical compounds having, as peptides do, an isoelectric point or being uncharged under the conditions used, by electrophoresis, wherein, contrary to the desired product, only the undesired by-products and contaminants come into contact with the matrix and which process gives excellent yields of the desired product in a very pure form.

Both the conception of said task itself and its solution involve inventive steps.

Figure 2:
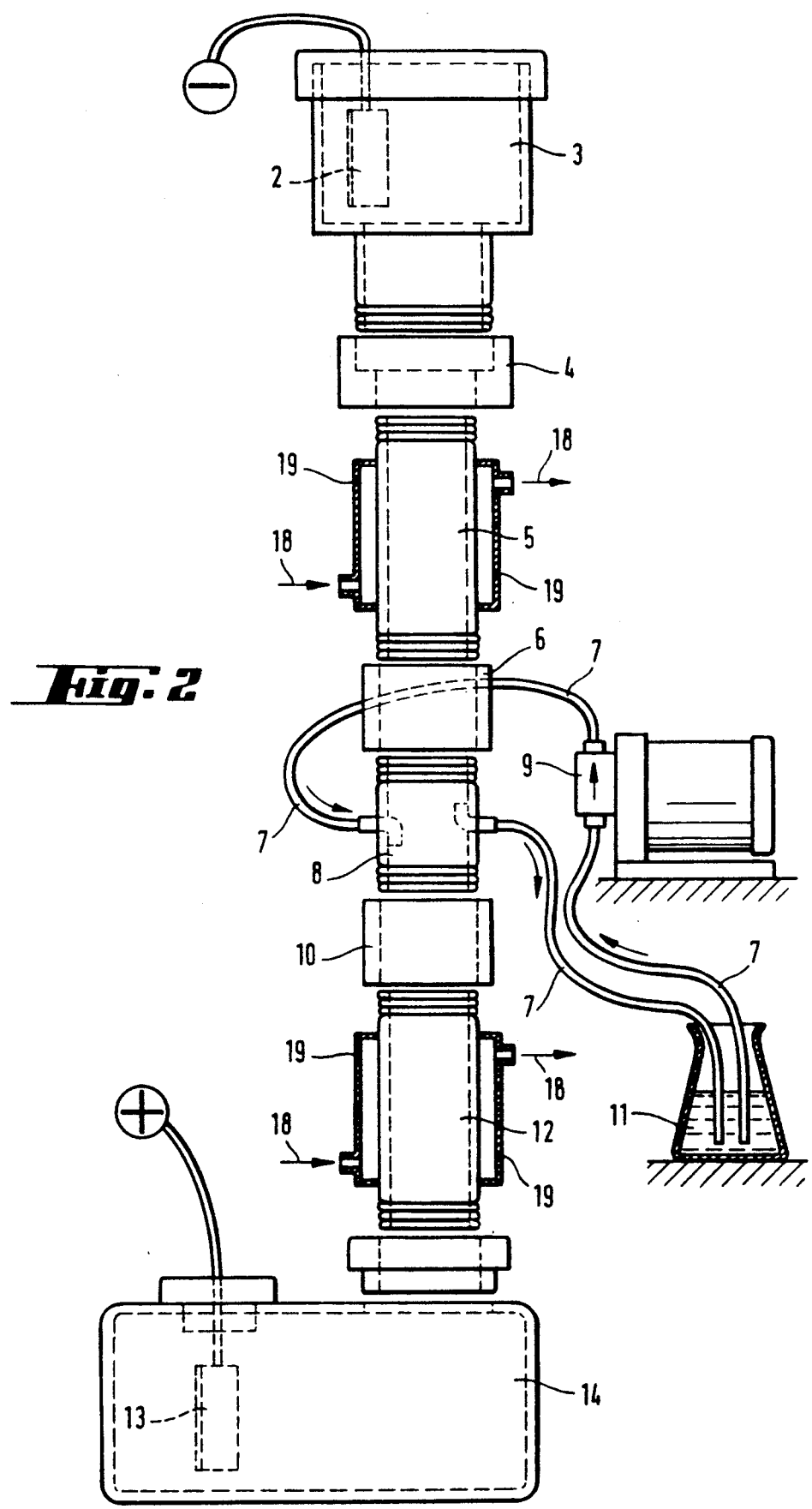
Figure 3:
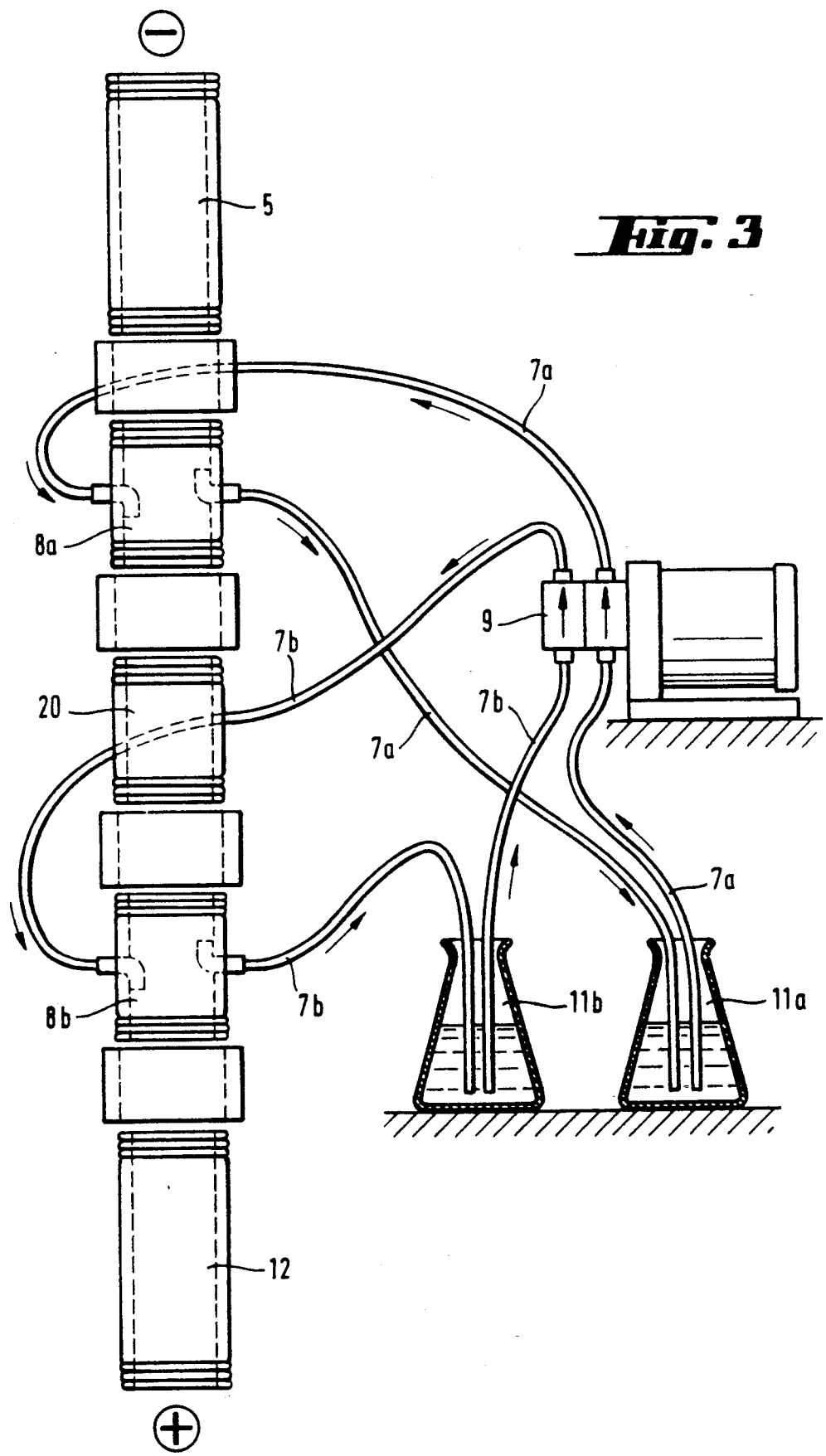
Figure 4:
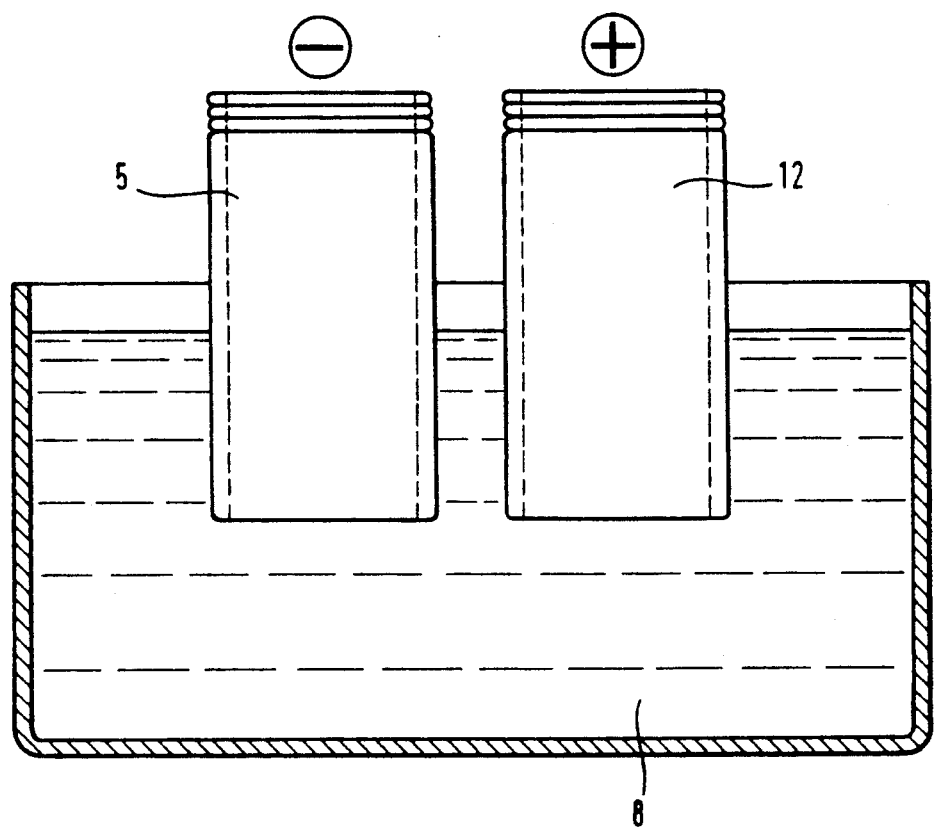
Figure 5:
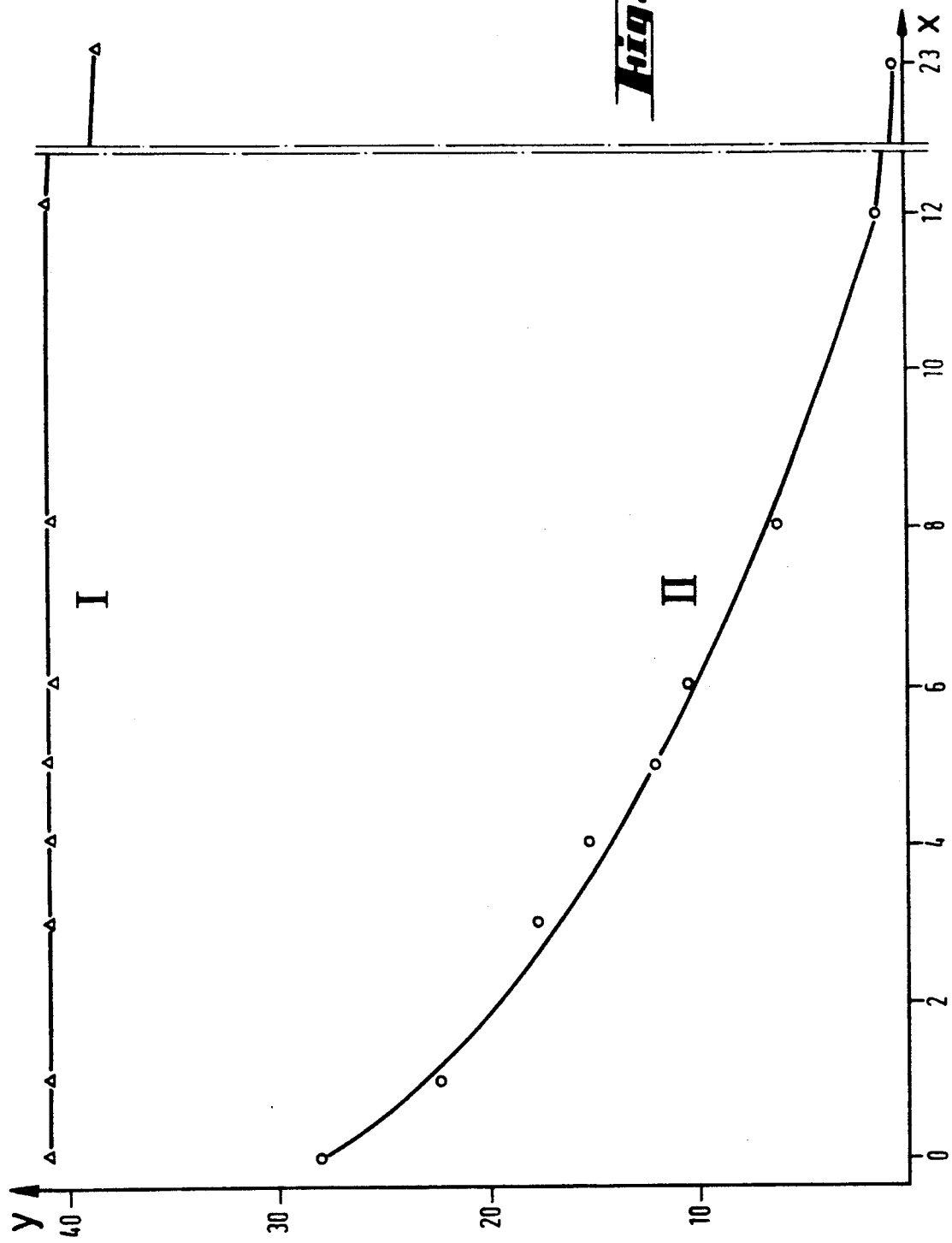
Figure 6:
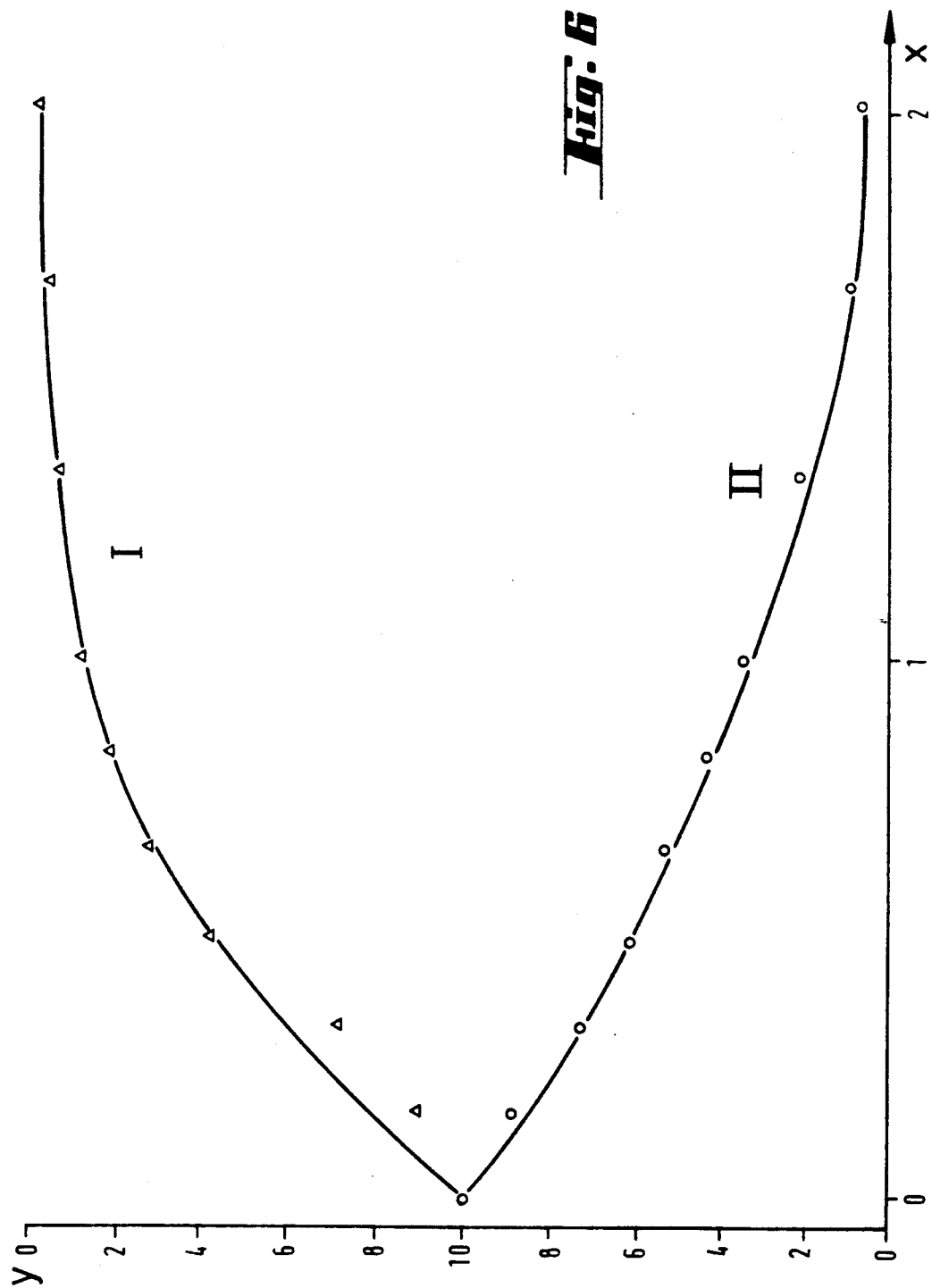
Figure 10:
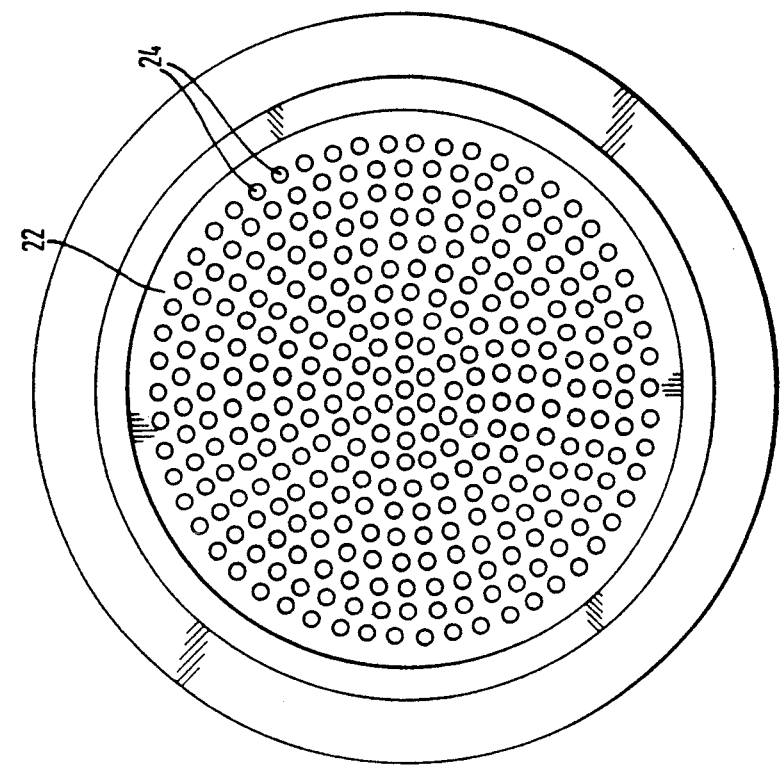
Figure 9:
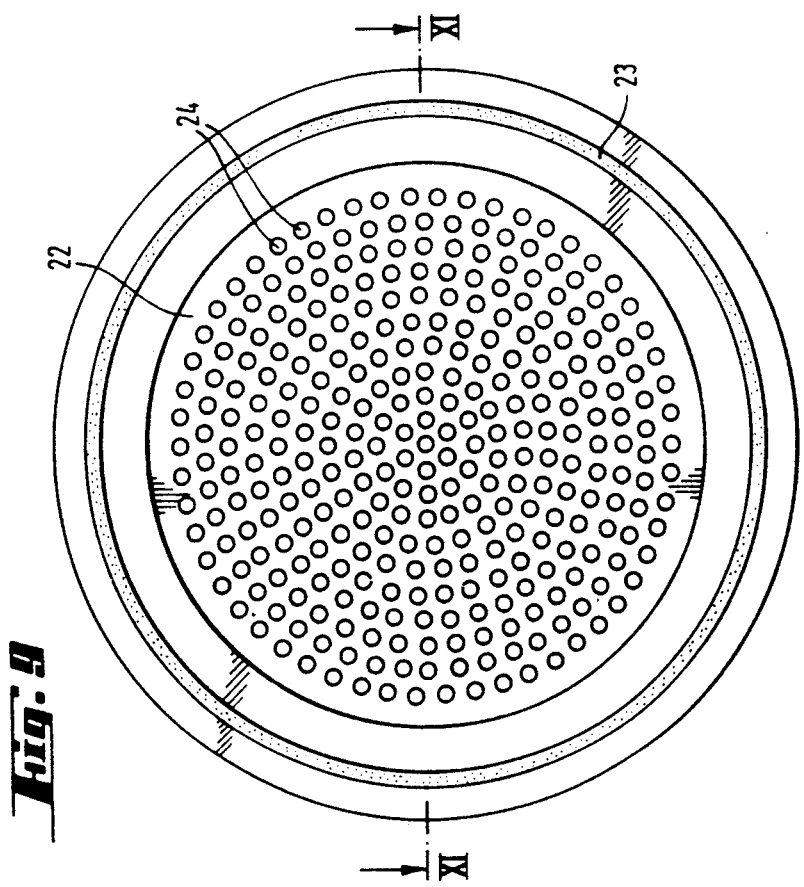
Figure 11:
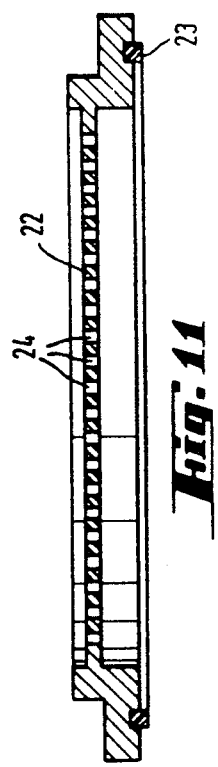
Figure 12:
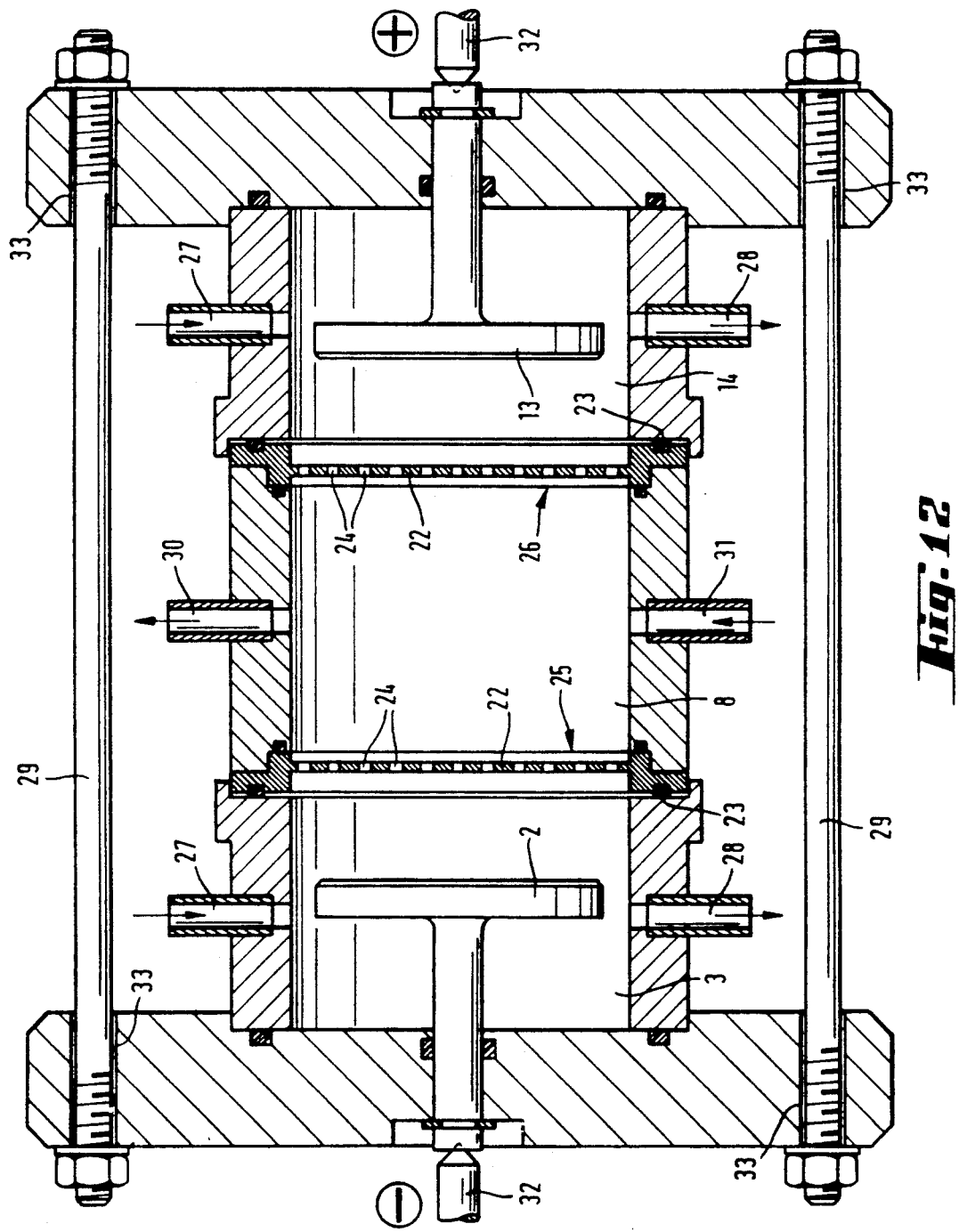

In the following, the invention will be described with reference to the accompanying drawings of which:

FIG. 1 is a schematic over all view of an apparatus which can be used to carry out the electrophoretic process according to the present invention, FIG. 2 is a schematic exploded view of parts of an apparatus as depicted in FIG. 1, FIG. 3 is a schematic exploded view of an alternative embodiment of an apparatus according to the present invention, FIG. 4 is a schematic view of the most essential parts of another alternative embodiment of an apparatus which can be used to carry out the process according to the present invention, FIG. 5, FIG. 6 and FIG. 7 are diagrams illustrating the success of electrophoretic separations according to the process of the present invention, FIG. 8 is a sectional view of a third alternative embodiment of an apparatus according to the present invention, FIG. 9 is a view from below at a perforated disque which is a part of the apparatus depicted in FIG. 12, FIG. 10 is a view from above at said disque, FIG. 11 is a cross-sectional view taken along line XI—XI of FIG. 9, and FIG. 12 is a cross-sectional view of a fourth alternative embodiment of an apparatus according to the present invention.

The present invention relates to an isoelectric focusing electrophoretic process for the separation and purification of an amphoteric or neutral chemical compound, soluble in a solvent suitable for said process, from one or more electrically charged chemical compound(s), soluble in said solvent, said process being carried out by using an electrophoretic apparatus, wherein the electric flow, i.e. the electric field, passing through the electrophoretic matrix, is coupled to a hydraulic flow 7, 8 and 11 (cf. the figures), the direction of said electric flow being different from that of said hydraulic flow, said hydraulic flow comprising a solution of said compound in said solvent and segmenting said matrix into two parts, one part, 5 or 25, being located at the cathodic side and the other, 12 or 26, being located at the anodic side of said electric flow, characterized in that said amphoteric or neutral chemical compound is kept in an isoelectric or uncharged state within the hydraulic flow, and said charged chemical compound(s) is (are) removed from the hydraulic flow by the electric flow into at least one of said parts of said matrix, or by way of at least one of said parts into at least one of the electrolyte solution reservoirs 3 and 14, said parts, independently of each other, representing immobilized pH-gradients 5 and 12, each having conductivity and both buffering and titrant capacity in its pH-interval, or amphoteric isoelectric immobilized pH-membranes 25 and 26, each having conductivity and both buffering and titrant capacity at a specific pH-value.

The amphoteric or neutral compound, kept in an isoelectric or uncharged state, is a chemical compound having no electrical net charge or being neutral under the conditions of the purification process and at the time when the separation from the undesired accompanying chemical compound(s) actually takes place. It is preferably a protein, enzyme or smaller peptide having at least two amino acids or a compound containing a peptide- or protein moiety, e.g. a glycoprotein, but also a nucleic acid, complex lipid or complex carbohydrate.

Contrary thereto, an electrically charged chemical compound is a chemical species having an electrical charge under the conditions of the purification process and at the time when the separation from the desired chemical compound actually takes place, e.g. a protein, enzyme or smaller peptide being charged, i.e. non-isoelectric, and also a salt, e.g. an alkali metal salt, e.g. sodium chloride.

A solvent suitable for the process according to the present invention is any solvent solubilizing the desired chemical compound and allowing for the necessary electric flow, e.g. water or a mixture of water with a suitable alcohol, e.g. a lower alkanol, for example methanol or ethanol, or an aqueous solution containing urea, detergents or any other water-miscible organic or protic solvent.

The electric flow is generated by the power supply 1. Any voltage the system can tolerate may be used, e.g. 100 to 10,000 volt, especially 500 to 10,000 volt, preferably 500 to 5000 volt, e.g. 500, 1000, 5000 or even 10,000 volt, provided the generated heat can be dissipated by proper cooling. At equilibrium, typical values are e.g. 1000 volt, 3 mA and 3 W or 500 volt, 10 mA and 5 W.

The electrophoretic matrix is a carrier for the electrophoretic separation.

The hydraulic flow is generated e.g. by a pump, by stirring or by rotating the flow chamber 8 around a suitable axis and comprises as liquid phase a solution containing the mixture to be separated.

The direction of the hydraulic flow is at any suitable angle, e.g. 5° to 90°, especially 30° to 90°, preferably about perpendicular (orthogonal), to the direction of the electric flow.

An immobilized pH-gradient as contained e.g. in cylinders 5 or 12 comprises a stable pH-function on an electrophoretic matrix, e.g. a gel. Immobilized pH-gradients comprise a pH-interval which is generated in a manner known per se, e.g. by means of an overlayered density gradient and polymerization (cf. Application Note 321, dated August 1982, of LKB-Produkter AB, Box 305, S-16126 Bromma, Sweden), e.g. by mixing equal volumes of the two starting solutions A and B described below in a gradient mixer, e.g. the "Micro-Grad Gradient Maker" supplied by LKB-Produkter AB, the outlet of said mixer being connected with cylinder 5 or 12. Starting solution A is an acidic, dense solution and contains buffering Immobilines (registered trademark, used in the following without indication) or an equivalent thereof, non-buffering Immobilines or an equivalent thereof, Ampholines (registered trademark, used in the following without indication) or an equivalent thereof, acrylamide, N,N'-methylene-bis-acrylamide, glycerol, water and suitable polymerization catalysts. Starting solution B is a basic, light solution containing buffering Immobilines, non-buffering Immobilines, Ampholines, acrylamide, N,N'-methylene-bis-acrylamide, water and suitable polymerization catalysts, but no glycerol.

Amphoteric isoelectric immobilized pH-membranes are distinguished from the immobilized pH-gradients in that they do not comprise a pH-interval but have throughout the membrane the same pH-value. The manufacture of the membranes is similar to, but even simpler than the manufacture of the pH-gradients because no gradient mixer is required and no glycerol is necessary for preparing a density gradient.

The membranes are manufactured by polymerisation, preferably around neutral pH, at 50° C. in a forced-ventilation oven for 1 hour, of a solution of monomers (in general 10–15% T and 3–4% C) containing variable amounts of buffering and titrant Immobilines in the ratios needed to generate the desired isoelectric point together with Ampholines, suitable polymerisation catalysts and water. It is essential that the membranes have a good buffering capacity at their isoelectric point in order to prevent electroendosmosis, a term denoting bulk liquid flow through the membrane caused by the presence or acquisition of a net electrical charge. However, the Immobiline molarity should preferably not exceed 50 mM of each Immobiline in the membrane.

Ampholines are low-molecular-weight amphoteric substances, i.e. ampholytes, which contrary to Immobilines are not fixed to the acrylamide/N,N'-methylene-bis-acrylamide polymer and are therefore able to contribute to the electrical conductivity. Mixtures of many amphoteric substances such as amino acids and peptides and some amphoteric and non-amphoteric buffer components can act as suitable ampholytes. However, the great majority of iso-electric focusing experiments are performed with the aid of commercial ampholyte mixtures. The most widely used of these, is marketed by LKB Produkter AB under the brand name Ampholines. They consist of synthetic mixtures of polyaminopolycarboxylic acids with molecular weights mostly in the region of 300–600. Other products can be used which contain sulphonic or phosphonic acid groupings in addition to the amino and carboxylic acid groups. These products (Servalyts ®, Serva-Feinbiochemica GmbH; Biolytes ®, Bio-Rad Laboratories; Pharmalytes ®, Pharmacia AB) have recently been compared with the Ampholines and shown to have a similar performance.

Immobilines are acrylamide derivatives with the general structure

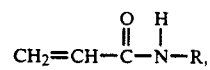

where R contains either a carboxylic acid or a tertiary amino group. Immobilines are designed for co-polymerization with acrylamide and N,N'-methylene-bis-acrylamide in order to produce immobilized pH-gradients. Each derivative has a defined and known pK-value. Acrylamide may be replaced e.g. by methacrylamide and N,N'-methylene-bis-acrylamide may be replaced by any other suitable crosslinker, e.g. suitable other acrylamide derivatives. N-(3-Dimethylamino-propyl)-methacrylamide having a pK-value of 9.5 may be mentioned as an example of a methacrylamide derivative being analogous to an Immobiline. After co-polymerisation the Immobilines are covalently bound, i.e. immobilized, and do not contribute anything to the conductivity of the pH-gradient or pH-membrane. However, the Immobilines contribute to the buffering and titrant capacity.

Preferably, the pH-gradients and pH-membranes are cast somewhere within a pH-range from about 3 to about 10, depending on the Immobilines and Ampholines available. If the compound of interest is amphoteric, the pH-values in the two gel extremities facing the flow chamber 8 have to be set just above and below or equal to the isoelectric point of said amphoteric substance with the precision required to keep it in the isoelectric state all the time. Said precision and the difference between the pH-values in said gel extremities, i.e. the width in terms of pH-units of the gap in between said gel extremities, depends on the resolving power needed, i.e. on the isoelectric points of the contaminants which have to enter the gel, i.e. at least pass the gel. In order to achieve the highest possible resolving power, the pH-values in said gel extremities can be the same and equal to the isoelectric point of the desired compound. In that case it is advantageous to prevent losses of the desired compound which might occur by way of diffusion by inserting some appropriate mechanical means, e.g. a suitable millipore filter, between gel and hydraulic flow. If the compound of interest is neutral, the pH-values in said gel extremities are chosen so that the contaminants have to enter the gel. Said contaminants may stay within the gel or leave it again and accumulate in the anodic and cathodic chambers 14 and 3. Suitable polymerization catalysts are e.g. N,N,N',N'-tetramethylethylenediamine (TEMED) and ammonium persulphate. Said catalysts are added shortly before starting mixing the dense and light solutions mentioned above. Other means for polymerization are e.g. riboflavin with ultraviolet light or gamma radiation.

In the gradient mixer, the basic, light solution is mixed into the acidic, dense solution which is simultaneously withdrawn into the outlet of the gradient mixer which is connected to the container 5 or 12. Thereby the obtained density gradient co-varies with the pH-gradient. The lower end of containers 5 and 12 is provisionally sealed, e.g. with parafilm. After the polymerization process is finished, the parafilm is removed. If the inside diameter of said container is too long it may be necessary to insert some support, e.g. a perforated plate, which is not removed, at the lower end of the container. At least those parts of the container coming in touch with the polymer have to be made of some material to which the polymer well adheres, e.g. of glass, in order to avoid the passage of some liquid between the wall of the container and the polymer. The containers 5 and 12 containing the immobilized pH-gradients are built into an apparatus according to the present invention, e.g. as shown in FIG. 1 and 2. Afterwards the gradients are properly washed to remove undesired substances, e.g. unbound Immobiline chemicals, catalysts and ungrafted monomers. Otherwise, due to the very low conductivity of the central portion of the gel as weak unbound anions and cations are electrophoretically depleted, the two salt fronts, accumulated towards the anodic and cathodic gel regions, are never able to leave the gel. In order to achieve good focusing, the primary, Immobiline gradient is overlayered with a secondary, carrier ampholyte driven pH-gradient. The apparatus according to the present invention is usually run with the flow chamber full of liquid for several hours, e.g. about five hours, till attainment of steady-state prior to sample application. Afterwards the flow chamber 8 and, if necessary, all other containers, coming in touch with the hydraulic flow, e.g. the sample reservoir 11, are emptied in order to remove noxious material leached out from the polymer, such as ungrafted monomers, and filled with the sample to be purified.

During the entire process according to the present invention the sample solution is vigorously stirred to prevent electrodecantation and kept at constant temperature. The pH-gradients in containers 5 and 12 are also kept at constant temperature. The temperature used depends inter alia on the solvent, the stability and the solubility of the desired substance. In water, it is normally kept at a fixed value between about 1° and 20° C., e.g. at 2° C.

The basic concept of the present invention is that of a mixed preparative technique, utilizing a liquid bed which may be a short one and which is coupled to two gel phases delimiting it, and is illustrated in the following example of the purification of a protein. The protein of interest is kept in an isoelectric state in the liquid phase, e.g. in a small, recycling chamber 8, while the impurities accompanying it are driven away either towards the cathode 2 or the anode 13 and eventually (but not necessarily) focussed in the gel phases 5 and 12, representing the pH-gradients (the numbers refer to the figures). The pH-gradients can be replaced by pH-membranes. Thus, in this modified isoelectric focusing technique, the protein of interest is not driven electrophoretically into the gel matrix (from which it would have to be recovered by an additional purification step), but is kept in an isoelectric state in the liquid stream (hydraulic flow) 7, 8 and 11 constituting the sample feed and only the (electrically charged) impurities are forced to focus in the gel phases 5 and 12, delimiting the liquid sample input, or to collect in one or both of the electrolyte reservoirs 3 and 14. Preferably, the pH-value within the hydraulic flow corresponds to the isoelectric point of the desired compound. Because the electrophoretic separation is performed in a pH gradient (isoelectric focusing), all the species having an isoelectric point within the pH-gradient 5 or 12 are driven by the voltage gradient into the particular zone where they exhibit zero net charge and in which they remain stationary as long as the electric field is applied. The difference compared with previous techniques is inter alia that the starting conditions are arranged in such a way that the component of interest is already isoelectric in the flow chamber 8 which constitutes the sample feed of the system. Therefore, the component of interest is not forced to migrate by the electric flow. Instead of using a conventional isoelectric focusing (IEF) system based on amphoteric buffers [cf. P. G. Righetti, Isoelectric Focusing: Theory, Methodology and Applications, Elsevier, Amsterdam, pp. 204-207 (1983)], in the process according to the present invention a more advanced version of it, an immobilized pH-gradient technique (IPG) [cf. P. G. Righetti, J. Chromatogr. 300, 165-223 (1984)] used.

A conventional isoelectric focusing (IEF) system would not be suitable for the process according to the present invention for the following reasons: a) IEF is not stable with time, in fact the pH gradient decays and is subjected to a progressive acidification (cathodic drift) [cf. P. G. Righetti and J. W. Drysdale, Ann. N.Y. Acad. Sci. 209, 163-186 (1973) so that the protein of interest would not be kept in the liquid phase, but would eventually move into the gel matrix; b) due to the fact that pH gradients are generated only in an approximate way in conventional IEF systems, it would be impossible to set the boundary conditions in the two gel extremities facing the flow-chamber 8 with the precision required to keep the chemical compound of interest having an isoelectric point just in the isoelectric state all the time, thus preventing it from leaving the liquid phase [hydraulic flow; 7, 8 and 11]. In contrast thereto, with immobilized pH-gradients (IPGs) and pH-membranes, it is in most cases possible to set the boundary conditions so that the anodic gel extremity facing the sample flow has a pH value just below the isoelectric point (pI) of the component of interest, while the respective cathodic gel extremity is set at a pH value just above the pI of the desired compound. Of course, the manufacture of suitable IPGs may be difficult in the comparatively rare cases where the desired substance has an extremely high or low pI. Said chemical compound, having an isoelectric point, will thus be isoelectric in this narrow pH gap delimited by the two immobilized pH-gradients or pH-membranes. If the compound of interest is amphoteric, this gap comprises normally 0.05 to 0.2 pH-units; however, gaps comprising down to 0.001 pH-units can be also achieved. It is also possible that the gap comprises 0 pH-units, i.e. the pH-values in said gel extremities correspond to the isoelectric point of the desired compound. This means that there is no pH-gap at all, but only a fluid gap between two gel phases. If the compound of interest is neutral, the pH-values in the gel extremities are not chosen in respect to the desired compound, but in respect to the undesired amphoteric or charged compounds, in the sense that said undesired compounds should not have an isoelectric point within said pH-gap. The neutral compound will never enter the pH-gradients, irrespective of the boundary conditions in the gel extremities facing the flow chamber 8. In addition to this precision in setting the boundary conditions, due to the unlimited stability of IPGs with time, it is automatically ensured that the pH gradient never drifts so that the isoelectric conditions for the chemical compound under purification will be constantly found in the hydraulic flow, especially in the flow-chamber 8, and not elsewhere, e.g. within the anodic or cathodic gel phases 12 and 5.

The process according to the present invention has at least the following major advantages: a) extremely high sample recoveries, approaching 100%, as the chemical compound (e.g. the protein) under purification never enters the gel phase, but is kept uncharged, e.g. in an isoelectric state, during the entire purification step in the liquid phase; b) large sample loads, as the compound to be purified, e.g. the protein feed, may be kept circulating between a separate reservoir 11 and the flow chamber 8 and only small amounts need be present at any given time in the electric field; c) a high resolving power, depending on how narrow the pH interval selected across the isoelectric point (pI) of the desired compound, e.g. protein, is; d) automatic removal of any salts or buffers accompanying the compound (e.g. the peptide or protein) of interest, which means that the present process can also be used for electrodialysis (desalting process). Especially the removal of monovalent ions of strong acids or bases, e.g. Na⊕ and Cl⊖, is very easy. For the removal of monovalent ions of weak acids and bases, e.g. ammonium and acetate, it is advantageous to use the amphoteric isoelectric Immobiline membranes described below or rather short pH-gradients, i.e. gradients comprising only a comparatively small pH-range, e.g. 0.5 to 1.0 pH-units, substantially removed from the pK-values of the respective weak acids and bases. The removal of multivalent ions, e.g. sulphate, phosphate and citrate, takes more time, possibly due to the interaction of these species with the Immobiline matrix, and is best carried out under outside pH-control, e.g. with a pH-stat, because otherwise, due to the faster removal of the monovalent counterion, the solution in chamber 8 can become rather acidic or alkaline. Rapid desalting of protein samples for a variety of uses, e.g. enzyme reactions or ligand binding studies, is one of the problems currently faced in biochemistry.

Any salt content in the sample feed (already at 1 mM concentration) inhibits the transport of non-isoelectric proteins, perhaps because of the much larger current fraction carried by the ions themselves as opposed to proteins. In addition, high salt levels in the sample reservoir may form cathodic and anodic ion boundaries, alkaline and acidic, respectively, which may hamper protein migration and even induce denaturation. In segmented (as well as in conventional) IPG gels, practically any level of salt present in the sample zone inhibits its electrophoretic transport. Therefore, the best way to efficiently eliminate protein impurities from an isoelectric component is to introduce an already desalted protein feed into the segmented IPG apparatus. However, elimination of protein impurities can be achieved, although at a slower rate, even in the presence of salts in the sample. In the latter case, salt levels should be kept at the minimum compatible with protein solubility (e.g. 5 mM or lower) and external pH control should be exerted (e.g. with a pH-stat) so as to prevent drastic pH changes in the sample feed, brought about by the generation of boundaries produced by the salt constituents. In quite a few cases, a minimum salt concentration might be needed in the sample phase during the electrophoresis for preventing protein aggregation and precipitation due to too low an ionic strength at or in the vicinity of the isoelectric point. For that purpose, an external hydraulic flow is used, replenishing the salt loss due to combined electric and diffusional mass transports (similar to the concept of Rilbes' steady-state rheoelectrolysis, H. Rilbe, J. Chromatography 159, 193–205[1978]).

The above-mentioned process may be carried out with one of the following electrophoretic apparatus belonging also to the subject of the present invention:

All of said electrophoretic apparatus basically comprise a flow chamber 8 connected with two containers 5 and 12 each of which is filled, independently of the other, with an immobilized pH-gradient or replaced by an immobilized pH-membrane, one of which gradients or membranes having at its extremity connected with the flow chamber 8 an isoelectric point just below or equal to the isoelectric point of the chemical compound to be purified and being connected at its other extremity to the anodic chamber 14 and the remaining pH-gradient or pH-membrane having at its extremity connected with the flow chamber 8 an isoelectric point just above or equal to the isoelectric point of said chemical compound to be purified and being connected at its other extremity to the cathodic chamber 3.

A schematic view of one of several possible modifications of this novel electrophoretic apparatus is given in FIG. 1. A flow-chamber 8 is connected to a sample reservoir 11 which, in principle, can hold any volume for processing via a pump 9 recirculating the feed through the electric field. In general, the pump 9 is operated at maximum speed, e.g. 5 ml/min. Perpendicular to the hydraulic flow 7, an electric field is activated between two plates 2 and 13, preferably made of platinum, which serves to electrophoretically remove from the flow chamber 8 any ion or non-isoelectric amphoteric species. The flow-chamber 8 is connected, e.g. via upper and lower O-ring seals 6 and 10, to two polyacrylamide gel cylinders 5 and 12, held in short glass tubes, fitted with jackets 19 for coolant flow 18 [19 and 18 are not shown in FIG. 1, but in FIG. 2]. The upper tube is connected, e.g. via a water-tight O-ring seal 4, to the cathodic chamber 3, containing in general a diluted base (e.g. 50 mM NaOH or ethanolamine, ethylendiamine, isoionic lysine or arginine), as is customary in conventional isoelectric focusing (IEF). The lower tube 12 bathes its extremity directly in an anodic chamber 14, in general containing a diluted (strong or weak) acid, such as acetic acid, phosphoric acid or sulphuric acid or isoionic aspartic or glutamic acid solutions, just as routinely used in standard IEF. Obviously, the O-ring seals may be replaced by any other suitable means for connecting the various parts of the apparatus.

The novel feature of the present fractionation technique is that the flow-chamber 8 is delimited by the extremities of a lower and a upper polyacrylamide gel representing immobilized pH-gradients or pH-membranes. Said pH-gradients are contained in the cylinders 12 and 5 which are preferably made from glass or another suitable material to which the gel is able to adhere by adhesive forces. By arranging the extremities of these two gel segments delimiting the flow-chamber 8 to have isoelectric points (pI) just below (on the anodic side) or equal to and just above (on the cathodic side) or equal to the isoelectric point of the desired compound, e.g. protein, under purification, this compound will in practice be titrated to its pI and as such will not be able to leave the hydraulic flow 8, 7 and 11. Conversely, all impurities having a different pI, e.g. proteinaceous impurities, accompanying the compound under purification will automatically be [at the pH-value prevailing in the flow chamber 8] either above or below their respective pIs, and thus be forced to leave the chamber 8 and focus either in the lower or upper segments 12 or 5 of the immobilized polyacrylamide gel or collect in the anodic or cathodic chambers 14 or 3. Given sufficient recycling time under a voltage gradient, all impurities leave the flow chamber 8 and the pure compound, e.g. isoelectric protein, is recovered from the flow chamber 8 and the sample reservoir 11 originally containing the feed. No further manipulations or sample extractions are needed, as the compound, e.g. protein, of interest stays all the time in the liquid phase and does not enter the gel.

The apparatus, which is assembled e.g. vertically or preferably horizontally, comprising the anodic and cathodic chambers 14 and 3, the gel cylinders 12 and 5, the seals 10, 6 and 4 and the flow chamber 8 is connected to a power supply 1. At equilibrium, typical values are 1000 V, 3 mA and 3 W, any other value being suitable for separations provided the generated heat can be removed by proper cooling. The sample flow-chamber 8 is provided by a means to keep it at a constant temperature, and/or the feed is kept in a larger, jacketed reservoir 11, coupled to a thermostat 17. It is advantageous to keep the sample vessel 11 under continuous, gentle stirring, otherwise, with time, a denser stratum could separate from a lighter one. Any pumping device 9, e.g. a peristaltic pump, is utilized for recycling, which is in general performed at maximum speed (e.g. 5 ml/min) so that the sample stays for as short a time as possible in the flow chamber 8, thus avoiding any risk of thermal denaturation. This is one of the simplest set-ups for operation. In principle, any other probe or metering device can be built around this apparatus if needed: e.g. a biosensors detection system, an immunoelectrophoretic equipment, a laser excited fluorescence detection equipment, any desired robotically coupled system, a device, e.g. a flowelectrode, for pH measurements and control, a device for radioisotop monitoring and/or a device, e.g. a flow-cell for conductivity monitoring, as needed. Obviously, for special purposes, the sample flow 7 could also be monitored in the UV, or visible, or by fluorescent observation, with the standard equipment coupled to chromatographic columns for following the rate of removal of some components in the mixture.

FIG. 2 shows a schematic extended view of about the same apparatus as depicted in FIG. 1 without showing the power supply 1, the stirrer 16 and the thermostat 17 depicted in FIG. 1, but showing, in addition to FIG. 1, the jackets 19 for coolant flow 18 around the gel cylinders 5 and 12, as well as the various components 3, 5, 6, 8, 10, 12 and 14 in the correct position for assembly, but not yet assembled. The coolant flow 18 is connected to a thermostat, e.g. 17, not shown in FIG. 2. Although not shown in FIG. 2 (cf. however FIG. 1) the sample reservoir 11 should also be kept at a constant temperature, e.g. 2° C., since the isoelectric points depend on the temperature. If desired, the flow chamber 8 may be also provided with jackets for coolant flow. FIG. 2, in addition to FIG. 1, also shows a preferred form for the flow chamber 8: the inlet and the outlet for the hydraulic flow 7 are bent, one towards cylinder 12 and the other towards cylinder 5. Container 12, although depicted with two screw-on-connections can be plunged directly into the anolyte solution in the electrode chamber 14.

FIG. 3 shows an apparatus suitable, after assembly of its components, for purifying two amphoteric compounds, e.g. two proteins, having different isoelectric points in the same apparatus and at the same time. Sample reservoirs 11a and 11b contain the initial feed which may be the same or different. Sample reservoir 11a is connected via some kind of tubing 7a with one of two flow chambers 8a. Sample reservoir 11b is connected via another tubing 7b with the second flow chamber 8b. The flow chambers 8a and 8b are separated from each other by an intermediate cylinder 20 containing an immobilized pH-gradient. The extremity of said intermediate pH-gradient directed to flow chamber 8b has a pH-value just higher, e.g. +0.05 pH-units, than the isoelectric point of the desired compound in flow chamber 8b or the same pH-value as the desired compound. The extremity of said intermediate pH-gradient directed to flow-chamber 8a has a pH-value just lower, e.g. −0.05 pH-units, than the isoelectric point of the desired compound in flow chamber 8a or the same pH-value as the desired compound. At the end of the IEF process, the desired purified species, e.g. proteins, are collected in chambers 8a/11a and 8b/11b, any charged contaminants having been removed.

For analytical purposes, an apparatus according to FIG. 1 may be used wherein, however, the flow chamber 8 is closed in as much as it is not connected to the sample reservoir 11. In this case, the apparatus may be arranged in horizontal position, immersed into the same coolant and rotated around its axis. Instead of rotating the entire apparatus, the sample in the flow chamber may be stirred, e.g. with a magnetic bar.

It is not only advantageous in the above-mentioned special case of a closed flow chamber but also in the usual case of an "open" flow chamber, having in-and outlets for the hydraulic flow, to use the electrofocusing apparatus in the horizontal position with said in- and outlets in vertical position, the outlet being situated above the inlet. In the vertical arrangement, air bubbles tend to accumulate in the upper portion of the flow chamber. This results in an uneven transport of impurities and hindrance of the electric current flow. For the removal of the air bubbles, the apparatus has to be disassembled and positioned horizontally to completely remove the bubbles through the outlet stream. Furthermore, the lower IPG segment, immersed in the lower electrolyte reservoir (in general the anode), tends to swell. This forces the gel to protrude from the supporting tube and eventually to detach from the glass walls and fall out of its lodging. These problems are eliminated by a horizontal apparatus, e.g. as depicted in FIG. 8, provided with filters 21 at all extremities of the IPG segments, for blocking the Immobiline gel phases in situ. The filters 21 are stretched in situ by an O-ring sitting on an annular ledge in the outer tube.

In FIGS. 1 to 3, the immobilized gel containers 5 and 12 are situated opposite to each other. It is, however, also possible to arrange them parallel to each other as shown in FIG. 4. Such arrangement is especially suitable for large scale purification since more than two containers 5 and 12, e.g. 4, 6 etc., may be immersed into the flow chamber 8.

For most purposes the process and the apparatus can be improved by replacing at least one of the pH-gradients by amphoteric isoelectric immobilized pH-membranes. Said membranes may be regarded as very short pH-gradients covering only a very narrow pH-interval. Ideally, said pH-interval comprises zero pH-units. Furthermore, the difference between the pH-values in the extremities of the pH-gradients of pH-membranes, delimiting the flow chamber 8, may be also reduced to zero, i.e. the flow chamber may be delimited e.g. by two membranes having the same pH-value which is identical to the isoelectric point of the desired compound. This fact is surprising and facilitates the method in that two identical membranes can be prepared instead of membranes differing from each other. The use of pH-membranes instead of pH-gradients has the additional advantage of being cheaper. Furthermore, the generated heat may be removed more easily. Therefore, pH-membranes 25 and 26 will in most cases be preferred when large scale purifications have to be carried out.

The invention relates also to an apparatus suitable for being used in an isoelectric focusing electrophoretic process as herein described, said apparatus comprising a flow chamber 8 connected directly or indirectly either.
a) with two containers 5 and 12 each of which is suitable for being filled with and containing an immobilized pH-gradient, or
b) with two devices for taking up immobilized pH-membranes 25 and 26, or
c) with one container according to a) above and with one device according to b) above, one of which containers or devices being connected at its other extremity to the anodic chamber 14 and the remaining container or device being connected at its other extremity to the cathodic chamber 3.

The following examples illustrate the invention without limiting it in any way.

ABBREVIATIONS

A: Ampere
C: (if used to describe the gel composition) percentage (by weight) of total monomer T (cf. below) which is due to the crosslinking agent N,N'-methylene-bis-acrylamide having the formula $CH_2=CH-CO-NH-CH_2-CO-CH=CH_2$
IPG: immobilized pH-gradient
pI: isoelectric point
T: total concentration [g/100 ml, i.e. weight per volume per cent] of acrylamide and N,N'-methylene-bis-acrylamide
TEMED: N,N,N',N'-tetramethylethylenediamine
V: Volt
W: Watt.

EXAMPLE 1

Purification of a protein mixture

The experimental set-up is as in FIG. 1 and 2. The lower IPG segment 12 having a total volume of 26 ml contains a pH 3.5–7.2 range (7% T, 4% C)-matrix and 1% carrier ampholytes in about the same pH interval and is prepared from an acidic dense solution and a basic light solution by means of a suitable gradient mixer as follows:

The acidic dense solution is prepared from a mixture of 685 μl of pK 3.6, 223 μl of pK 4.6, 226 μl of pK 6.2, 118 μl of pK 7.0 and 154 μl of pK 8.5 Immobilines (from stock 0.2M solutions), 0.6 ml Ampholine ® pH 3.5–7.0, 3.1 ml stock (30% T, 4% C)-acrylamide and 3.6 ml glycerol by adding water to 13 ml. The basic light solution is prepared from a mixture of 124 μl of pK 3.6, 511 μl of pK 4.6, 347 μl of pK 6.2, 139 μl of pK 7.0, 310 μl of pK 8.5 and 238 μl of pK 9.3 Immobilines, 0.6 ml Ampholine pH 3.5–7.0 and 3.1 ml of stock (30% T, 4% C)-acrylamide by adding water to 13 ml. Once transferred to a suitable two-chamber-gradient-mixer, 10 μl of TEMED and 13 μl of 40% ammonium persulphate are added to each of the above-mentioned solutions.

The outlet of the gradient mixer is connected with chamber 12 the lower end of which is provisionally closed, e.g. by parafilm, until the polymerization process is finished. Polymerization proceeds for about 1 hour at 50° C. (or for 2 hours at 37° C.).

The upper IPG segment 5 (26 ml total volume) contains a pH 7.4–10.0 range, (7% T, 4% C)-matrix and 1% carrier ampholytes in the same pH-span and is prepared from the below-mentioned solutions a) and b) as follows:

a) The acidic dense solution (pH 7.4) is prepared from a mixture of 506 μl of pK 3.6, 387 μl of pK 7.0, 361 μl of pK 8.5 and 46 μl of pK 9.3 Immobilines (from stock 0.2M solutions), 0.6 ml Ampholine pH 7–10, 3.1 ml stock (30% T, 4% C)-acrylamide and 3.6 ml glycerol by adding water to 13 ml.

b) The basic light solution (pH 10) is prepared from a mixture of 93 μl of pK 3.6, 335 μl of pK 7.0, 362 μl of pK 8.5 and 289 μl of pK 9.3 Immobilines, 0.6 ml Ampholine pH 7–10 (all Ampholines from stock 40% solutions) and 3.1 ml of stock (30% T, 4% C)-acrylamide by adding water to 13 ml.

Once transferred to the gradient mixer, solutions a) and b) are each added with catalysts (TEMED and ammonium persulphate, in this order) as above.

The outlet of that gradient mixer is connected with chamber 5 the lower end of which is provisionally closed.

After the polymerization is complete the means used for provisionally closing chambers 5 and 12 are removed and said chambers containing the thus prepared IPG-gels are built into the electrophoretic apparatus depicted in FIG. 1. All non-amphoteric ions (ungrafted Immobilines, catalysts, buffers, etc.) are removed from the gel, prior to sample application, by pre-running for 5 hours at 5 W/1000 Volt. Thus the flow chamber 8 is confined to a narrow pH interval (pH 7.2–7.4) centred on the pI (7.30) of human adult hemoglobin (pI typical of human adult hemoglobin A [HbA] in an IPG gel at 10° C.). 70 mg total lystate from a heterozygous from human adult hemoglobin C [HbC] (containing ca. 60% HbA and 40% HbC), dissolved in 25 ml of 0.5% carrier ampholytes pH 6–8 are recycled in the prefocused apparatus under 1000 Volt constant. At 30 minute intervals 30 μl are sampled and kept at 4° C. for subsequent analysis. The experiment is terminated with the last sampling after 23 hours. The aliquots are analyzed in a (5% T, 4% C)-IPG gel in the pH 6.5–8.5 span. The results obtained by densitometric scans of the peaks of HbA and HbC with a laser densitometer (provided by LKB) are presented in FIG. 5 depicting along the x-axis the time [hours] and along the y-axis the amount [mg] of HbA and HbC. Curve I (triangles) refers to HbA and curve II refers to HbC. It is seen that, while HbA stays constant for the duration of the experiment, HbC is progressively removed till, at 23 hours, it cannot any longer be detected. After 12 hours of recycling, HbA is at least 95% pure while, after 23 hours, it is more than 99.5% pure.

EXAMPLE 2

Removal of dyes from a protein

In order to evaluate the performance of the apparatus depicted in FIG. 1 as an electrodialysis unit, the kinetics of removal of colored dyes (in the form of salts) from protein mixtures are evaluated. In the anodic arm 12 an IPG pH 3.5–7.2 gel and in the cathodic arm 5 and IPG pH 7.4–10 gel is polymerized. Thus the feed is kept at a pH between 7.2 and 7.4. The feed comprises a solution of 40 mg of purified human adult hemoglobin A in 0.5% Ampholine pH 6–8 added with 10 mg of an acidic dye (bromophenol blue) and with 10 mg of a basic dye (toluidine blue) (25 ml total volume). The removal of said dyes subjected to 1000 V constant is followed by sampling 30 μl at given time intervals from the sample reservoir and assessing the residual amounts by spectrophotometric readings at 600 nm. The results are shown in FIG. 6, depicting along the x-axis the time [hours] and along the y-axis the amounts [mg] of the two dyes. Curve I (triangles) shows the cathodic migration of toluidine blue and curve II refers to the anodic migration of bromophenol blue. As shown in FIG. 6, after 2 hours essentially all of the dyes has been removed from the flow chamber, leaving behind the desalted hemoglobin sample. The rate of withdrawal seems to follow a first order reaction kinetic, as a plot (not shown) of log concentration vs. time is linear. The shape of the toluidine blue curve I is initially steeper than that of bromophenol blue, but the measurements are complicated by the fact that this dye seems to consist of a family of three components, as three blue zones were seen migrating in the upper gel.

EXAMPLE 3

Protein Desalting 30 ml of a solution of human adult hemoglobin A (HbA) are rendered 50 mM in NaCl and recycled in the apparatus depicted in FIG. 1 at 10 W constant and at 2° C. The recycling chamber is delimited by a pH 7.2 floor and a pH 7.4 ceiling. The recycling speed is 10 ml/min. At the given time intervals, 2 ml aliquots are harvested, thermostated at 25° C. and monitored with an Analytical Control conductivity meter 101 fitted with an Orion conductivity cell. The conductivity measurements are converted into residual millimoles of NaCl. Desalting is essentially completed in two hours. The kinetics of desalting of HbA are shown in FIG. 7 depicting along the x-axis the time [hours] and along the y-axis the quantity [millimole] of sodium chloride.

EXAMPLE 4

Purification of N-acetyl-Eglin C a) The isoelectric point of N-acetyl-Eglin C (pI=5.5) is determined on Ampholine PAG-plates pH 3.5–9.5, 5% T, 3% C, 2.2% Ampholine concentration.

Ca. 350 μg total protein are applied in each pocket (in volumes up to 20 μl) and then focusing is performed at 10 W limiting, 10 mA, and 1000 V at equilibrium. The analytical runs are in general finished within 2 hours and then the gels are fixed and stained with Coomassie Blue.

The fixing solution is prepared by dissolving 15 g trichloroacetic acid in double distilled water and adding double distilled water up to a total volume of 100 ml.

The staining solution is prepared by dissolving 0.46 g of Coomassie Blue R 250 in 400 ml of the below-mentioned destaining solution. The obtained solution is heated to 60° C. and filtered before use. The above-mentioned destaining solution is prepared by adding double distilled water to 500 ml of ethanol up to a total volume of 1000 ml (solution I), by adding double distilled water to 80 ml of acetic acid up to a total volume of 1000 ml (solution II) and mixing solutions I and II in a ratio of 1:1 (v/v) before use.

b) For the manufacture of two amphoteric, isoelectric Immobiline membranes, pH 5.5, 10.512 ml of a 0.2M solution of Immobiline pK 4.6 and 9.664 ml of a 0.2M solution of Immobiline pK 9.3 are mixed and diluted with double distilled water to a total volume of 30.0 ml. The pH-value of the solution thus obtained is determined by means of a pH-meter to be 5.5. To said solution 40.0 ml of solution A (cf. below), 1.5 ml Ampholine pH 5–7, 96 μl TEMED, 120 μl of solution B (cf. below) and double-distilled water up to a total volume of 120.0 ml are added. The above-mentioned solution A is prepared by dissolving 28.8 g acrylamide and 1.2 g N,N'-methylene-bis-acrylamide in double distilled water and adding water up to a total volume of 100 ml. The above-mentioned solution B is prepared by dissolving 400 mg ammonium persulphate in 880 μl of double distilled water.

60.0 ml of the obtained solution are filled into each of two apparatus described below (cf. c) and polymerised at 50° C. for one hour.

c) The apparatus mentioned above used for preparing the membranes comprises a plate made from an inert material, e.g. polytetrafluorethylene (Teflon ®), which does not or only to a negligible degree adhere to the polymerisate. On said plate a round perforated disque

(22) is placed which is separated from said plate by a ring-shaped gasket (23) having a diameter of 9 cm and a height of 1 mm. FIG. 9 shows the view from below at said disque, FIG. 10 the view from above and FIG. 11 the cross sectional along view line XI—XI depicted in FIG. 9. The solution to be polymerised is filled through the holes 24 of the perforated disque.

d) The membranes obtained according to the procedure described above together with the perforated carrier plates 22 are then built into a cylinder having an inner diameter of about 9.5 cm and a height between the membranes of about 3 cm. Said cylinder is fitted with an inlet 31 and an outlet 30 opposite to each other for the hydraulic flow 7 and is used as flow chamber 8. If desired a millipore filter (8 μm) made from cellulose-acetate or 6,6-polyamide (Nylon) or something like that, e.g. a polypropylene filter, may be placed between the pH-membranes 25 and 26 and the hydraulic flow 7 preventing the substance to be purified (e.g. N-acetyl-Eglin C) from direct contact with the isoelectric membranes. The entire electrofocusing apparatus is assembled wherein the above-mentioned cylinder with the built-in membranes replaces the flow chamber 8 and the immobilized pH-gradients 5 and 12. Preferably, said cylinder is used in the horizontal position with the in- and outlet for the hydraulic flow 7 in vertical position, the outlet being situated above the inlet. The advantage of said horizontal arrangement in comparison to the vertical assembly is that air bubbles are spontaneously removed.

FIG. 12 shows a cross-sectional view of the assembled apparatus. A cylindrical tube is segmented by the supported pH-membranes 22 into the cathodic chamber 3, the flow chamber 8 and the anodic chamber 14. The cathode 2 and the anode 13 are connected via plugs 32 to the power supply 1 [not shown]. The hydraulic flow 7 enters the flow chamber 8 via the inlet 31 and leaves it via the outlet 30. The electrolyte solution in the cathodic and anodic chambers may be renewed via the in- and outlets 27 and 28. The various parts of the apparatus are held together by means of four thread poles 29 which are inserted through the holes 33.

e) The assembled electrofocusing apparatus is prerun for 1 hour at 500 volt, 25 mA and 10 W in a cold room (+5° C.) with the flow chamber full of liquid but without the N-acetyl Eglin C-sample to be purified. Then, the flow chamber is emptied and filled with the sample to be purified.

f) 1 g of the sample containing recombinant DNA-N-acetyl Eglin C (purity: 80%, prepared according to European patent application no. 146 785) is dissolved in 100 ml of 0.2% carrier ampholytes pH 5-7 and recycled (20 ml/minute) in the prefocused apparatus under 500 Volt constant and 10 mA/5 W in a cold room (+5° C.). At 30 minute intervals 100 μl are sampled and kept at 4° C. for subsequent analysis. The experiment is terminated with the last sampling after 5 hours. The aliquots are analyzed in an Ampholine PAG-plate pH 3-5 - 9-5, 5% T, 3% C, 2.2% Ampholine concentration. It is seen that all impurities are removed after 3 hours of recycling.

If desired, the solutions in the cathodic 3 and anodic 14 chambers may be pumped to a waste line at a speed of e.g. 5 ml/minute and regenerated from big reservoirs.

EXAMPLE 5

Membranes Having Different Buffering Capacity

Analogs of the pI=5.50 membranes disclosed in Example 4 are prepared to incorporate a 10 mM, 40 mM or 100 mM concentration of the Immobilines.

While the 10 and the 40 mM "membranes" exhibit correct electroosmotic properties and yield accurate experimental pI values, the 100 mM surface exhibits much larger dispersion and shows anomalous flow profiles in the pH range surrounding the pI. It seems thus reasonable to set an upper molarity limit of about 50 mM of each Immobiline in the "membrane".

What is claimed is:

1. An isoelectric focusing electrophoretic apparatus suitable for carrying out an isoelectric focusing electrophoretic process for the separation and purification of a desired amphoteric chemical compound, soluble in a solvent suitable for said process, from one or more amphoteric chemical compounds, soluble in said solvent, the isoelectric points of which differ from the isoelectric point of the desired compound by at least 0.001 pH units, said process being carried out by using an electrophoretic apparatus, wherein the electric flow, passing through the electrophoretic matrix, is coupled to a hydraulic flow, the direction of said electric flow being different from that of said hydraulic flow, said hydraulic flow comprising a solution of said desired chemical compound in said solvent, said electrophoretic matrix being segmented into two parts by the hydraulic flow, said parts, independently of each other, representing immobilized pH-gradients (5) and (12), each having conductivity and both buffering and titrant capacity in its pH-interval, or amphoteric isoelectric immobilized pH membranes (25) and (26), each having conductivity and both buffering and titrant capacity at a specific pH-value, one part (5) or (25), being located at the cathodic side and the other, (12) or (26), being located at the anodic side, characterized in that said desired chemical compound is kept in an isoelectric state within the hydraulic flow (7), (8) and (11), and the undesired amphoteric chemical compounds are removed from the hydraulic flow by the electric flow into at least one of the two parts of said matrix, or through at least one of said parts into at least one of the electrolyte solution reservoirs (3) and (14), said apparatus comprising a flow chamber (8) connected directly or indirectly either a) with two containers (5) and (12) each of which is filled with an immobilized pH-gradient having conductivity and both buffering and titrant capacity in its pH-interval, or b) with two amphoteric isoelectric immobilized pH-membranes (25) and (26) having conductivity and both buffering and titrant capacity at a specific pH-value, or c) with one pH-gradient according to a) above and with one pH-membrane according to b) above, the isoelectric points in the extremities of the pH-gradients or membranes adjacent to the flow chamber (8) being equal to or just below the isoelectric point of the amphoteric chemical compound to be purified (anodic side) and equal to or just above the isoelectric point of said amphoteric chemical compound to be purified (cathodic side), one of which pH-gradients or pH-membranes being connected at its other extremity to the anodic chamber (14) and the remaining pH-gradient or pH-membrane being connected at its other extremity to the cathodic chamber (3).

2. An apparatus according to claim 1 wherein the flow chamber (8) is connected via a pump (9) with a sample reservoir (11).

3. An apparatus according to claim 2 fitted with a device for keeping at least one of the pH-gradients, pH-membranes and the sample at a constant temperature.

4. An apparatus according to claim 3 fitted by at least one of the following devices: a device for pH-measurements and control, a device for conductivity monitoring, a biosensors detection system, an immunoelectrophoretic equipment, a laser excited fluorescence detection equipment, a robotically coupled system, a device for radioisotop monitoring or a device for monitoring the sample solution in the UV, or visible or by fluorescent observation.

5. An apparatus according to claim 3 fitted with a device for the mechanical support of the pH-gradient gel in containers (5) and (12) or of the gel in the pH-membranes.

6. An apparatus according to claim 3 suitable for the simultaneous purification of two amphoteric or neutral compounds comprising two separate flow chambers (8a) and (8b) separated from each other by an intermediate immobilized pH-gradient (20) or one or two pH-membranes.

7. An apparatus according to claim 3 arranged in such a position that air bubbles are removed from the flow chamber (8) by the hydraulic flow (7).

8. An apparatus according to claim 7 wherein the immobilized pH-gradients and pH-membranes have controlled buffering and titrant capacity and contain ampholytes in an amount ensuring sufficient conductivity.

9. An apparatus according to claim 3 wherein the immobilized pH-gradients and pH-membranes have controlled buffering and titrant capacity, pH-value and conductivity and can be prepared in a reproducible manner.

10. An apparatus according to claim 1 fitted with in-and outlets (27) and (28) for renewing the electrolyte solutions in the cathodic and anodic chambers (3) and (14).

11. An apparatus according to claim 30 comprising two and not more than two amphoteric isoelectric immobilized pH-membranes (25) and (26) each having controlled buffering and titrant capacity at a specific pH-value.

12. An apparatus according to claim 1, suitable for the purification of a peptide, protein or compound containing a peptide or protein moiety, each of which having an isoelectric point between pH 5 and 9.

13. An apparatus according to claim 1, suitable for separation of amphoteric chemical compounds the isoelectric points of which differ by at least 0.05 pH-units.

14. An apparatus according to claim 13 wherein the direction of the hydraulic flow is orthogonal to the direction of the electric flow.

15. An apparatus according to claim 14 wherein the direction of the hydraulic flow (7) is such that air bubbles are removed from the flow chamber (8).

16. An apparatus according to claim 13 wherein the immobilized pH-gradients have both buffering and titrant capacity in their pH-interval and contain an amount of ampholytes in the same pH-interval ensuring sufficient conductivity.

17. An apparatus according to claim 13 wherein the immobilized pH-gradients and pH-membranes have controlled buffering and titrant capacity, pH-value and conductivity and can be prepared in a reproducible manner.

18. An apparatus according to claim 17 wherein the desired compound is present in an aqueous solution.

19. An apparatus according to claim 1, wherein the pH-value within the hydraulic flow corresponds to the isoelectric point of the desired compound.

20. An isoelectric focusing electrophoretic apparatus suitable for carrying out an isoelectric focusing electrophoretic process for the separation and purification of a desired amphoteric chemical compound, soluble in a solvent suitable for said process, from one or more amphoteric chemical compounds, soluble in said solvent, the isoelectric points of which differ from the isoelectric point of the desired compound by at least 0.001 pH units, said process being carried out by using an electrophoretic apparatus, wherein the electric flow, passing through the electrophoretic matrix, is coupled to a hydraulic flow, the direction of said electric flow being different from that of said hydraulic flow, said hydraulic flow comprising a solution of said desired chemical compound in said solvent, said electrophoretic matrix being segmented into two parts by the hydraulic flow, said parts, independently of each other, representing immobilized pH-gradients (5) and (12), each having conductivity and both buffering and titrant capacity in its pH-interval, one part (5) being located at the cathodic side and the other, (12) or (26), being located at the anodic side, characterized in that said desired chemical compound is kept in an isoelectric state within the hydraulic flow (7), (8) and (11), and the undesired amphoteric chemical compounds are removed from the hydraulic flow by the electric flow into at least one of the two parts of said matrix, or through at least one of said parts into at least one of the electrolyte solution reservoirs (3) and (14), said apparatus comprising a flow chamber (8) connected with two containers (5) and (12) each of which is filled with an immobilized pH-gradient, one of which gradients having at its extremity connected with the flow chamber (8) an isoelectric point just below the isoelectric point of the amphoteric chemical compound to be purified and being connected at its other extremity to the anodic chamber (14) and the remaining pH-gradient having at its extremity connected with the flow chamber (8) an isoelectric point just above the isoelectric point of said amphoteric chemical compound to be purified and being connected at its other extremity to the cathodic chamber (3).

21. An isoelectric focusing electrophoretic apparatus suitable for being used in an isoelectric focusing electrophoretic process for the separation and purification of a desired amphoteric chemical compound, soluble in a solvent suitable for said process, from one or more amphoteric chemical compounds, soluble in said solvent the isoelectric points of which differ from the isoelectric point of the desired compound by at least 0.001 pH units, said process being carried out by using an electrophoretic apparatus, wherein the electric flow, passing through the electrophoretic matrix, is coupled to a hydraulic flow, the direction of said electric flow being different from that of said hydraulic flow, said hydraulic flow comprising a solution of said desired chemical compound in said solvent, said electrophoretic matrix being segmented into two parts by the hydraulic flow, said parts, independently of each other, representing amphoteric isoelectric immobilized pH membranes (25) and (26), each having conductivity and both buffering and titrant capacity at a specific pH-value, one part, (25), being located at the cathodic side and the other, (26), being located at the anodic side, characterized in that said desired chemical compound is kept in an isoelectric state within the hydraulic flow (7), (8) and (11), and the undesired amphoteric chemical compounds are removed from the hydraulic flow by the electric flow into at least one of the two parts of said matrix, or through at least one of said parts into at least one of the electrolyte solution reservoirs (3) and (14), said apparatus comprising a flow chamber (8) connected directly or indirectly with two devices for taking up immobilized pH-membranes (25) and (26), one of which is connected at its other extremity to the anodic chamber (14) and the remaining device is connected at its other extremity to the cathodic chamber (3).

* * * * *

UNITED STATES PATENT AND TRADEMARK OFFICE
CERTIFICATE OF CORRECTION

PATENT NO. : 5,082,548

DATED : January 21, 1992

INVENTOR(S) : Daniel M. Faupel, et al

It is certified that error appears in the above-identified patent and that said Letters Patent is hereby corrected as shown below:

Column 17, line 48, change "claim 30" to --- claim 1 -----

Signed and Sealed this

Fifth Day of October, 1993

*Attest:*

BRUCE LEHMAN

*Attesting Officer*  *Commissioner of Patents and Trademarks*